(12) United States Patent
Dobak, III

(10) Patent No.: US 6,364,899 B1
(45) Date of Patent: Apr. 2, 2002

(54) HEAT PIPE NERVE COOLER

(75) Inventor: John D. Dobak, III, La Jolla, CA (US)

(73) Assignee: Innercool Therapies, inc., San Diego, CA (US)

( * ) Notice: Subject to any disclaimer, the term of this patent is extended or adjusted under 35 U.S.C. 154(b) by 0 days.

(21) Appl. No.: 09/328,854

(22) Filed: Jun. 9, 1999

Related U.S. Application Data

(63) Continuation-in-part of application No. 09/262,805, filed on Mar. 4, 1999, and a continuation-in-part of application No. 09/215,040, filed on Dec. 16, 1998, and a continuation-in-part of application No. 09/215,038, filed on Dec. 16, 1998, and a continuation-in-part of application No. 09/103,342, filed on Jun. 23, 1998, now Pat. No. 6,096,068, and a continuation-in-part of application No. 09/052,545, filed on Mar. 31, 1998, and a continuation-in-part of application No. 09/047,012, filed on Mar. 24, 1998, now Pat. No. 5,957,963, and a continuation-in-part of application No. 09/012,287, filed on Jan. 23, 1998, now Pat. No. 6,051,019.

(51) Int. Cl.[7] .................................................. A61F 7/12

(52) U.S. Cl. ..................... 607/113; 607/104; 607/105; 606/20; 606/21; 606/22; 606/23

(58) Field of Search .......................... 607/96, 101, 105, 607/106, 107, 113, 114; 606/20, 21, 22, 23, 24, 25, 26

(56) References Cited

U.S. PATENT DOCUMENTS

| 2,672,032 A | | 3/1954 | Towse |
| 3,425,419 A | | 2/1969 | Dato |
| 5,121,754 A | | 6/1992 | Mullett |
| 5,190,539 A | | 3/1993 | Fletcher |
| 5,207,674 A | * | 5/1993 | Hamilton ...................... 606/20 |
| 5,269,369 A | | 12/1993 | Faghri |
| 5,403,281 A | | 4/1995 | O'Neill |

(List continued on next page.)

FOREIGN PATENT DOCUMENTS

| WO | WO 97/25011 | 7/1997 |
| WO | WO 98/26831 | 6/1998 |
| WO | WO 98/31312 | 7/1998 |
| WO | WO 91/05528 | 5/1999 |
| WO | WO 99/37226 | 7/1999 |
| WO | WO 99/48449 | 9/1999 |
| WO | WO 99/66970 | 12/1999 |
| WO | WO 99/66971 | 12/1999 |
| WO | WO 00/09054 | 2/2000 |
| WO | WO 00/10494 | 3/2000 |
| WO | WO 00/38601 | 7/2000 |
| WO | WO 00/47145 | 8/2000 |
| WO | WO 00/48670 | 8/2000 |

OTHER PUBLICATIONS

Apkarian, Vania A., A Cryogenic Device For Reversibly Blocking Transmission Through Small Regiosn Of The Spinal Cord White Matter; 1989. Journal of Neuroscience Methods.*

(List continued on next page.)

Primary Examiner—R. Kearney
(74) Attorney, Agent, or Firm—Mark D. Wieczorek

(57) ABSTRACT

The invention provides a method and apparatus for producing reversible focal hypothermia of the nervous system to control chronic pain. Nerve conduction is blocked by mild cooling (0 to 25° C.), or hypothermia. At these temperatures, nerve tissue is not destroyed and recovers completely when cooling is terminated, such that the treatment is reversible. By blocking conduction in pain nerves, pain sensation is eliminated in a manner analogous to drugs such as lidocaine that also block nerve conduction to provide anesthesia. The invention can be applied to a variety of conditions such as urge incontinence, muscle spasticity, and epilepsy. Many of these disorders are mediated by nerve and nervous tissue that could be interrupted by cooling. In addition, neurologic dysfunction found in multiple sclerosis may improve by cooling of the nerves. The method and apparatus may be used to cool areas of the nervous system affected by multiple sclerosis to allow more normal functions.

12 Claims, 8 Drawing Sheets

U.S. PATENT DOCUMENTS

| | | | |
|---|---|---|---|
| 5,417,686 A | 5/1995 | Peterson |
| 5,486,208 A | 1/1996 | Ginsburg |
| 5,571,147 A | 11/1996 | Sluijter et al. |
| 5,591,162 A | 1/1997 | Fletcher |
| 5,624,392 A | 4/1997 | Saab |
| 5,643,197 A | 7/1997 | Brucker et al. |
| 5,643,330 A | 7/1997 | Holsheimer |
| 5,676,691 A | 10/1997 | Friedman |
| 5,837,003 A | 11/1998 | Ginsburg |
| 5,879,329 A | 3/1999 | Ginsburg |
| 5,899,899 A | 5/1999 | Arless |
| 5,957,963 A | 9/1999 | Dobak, III |
| 5,989,238 A | 11/1999 | Ginsburg |
| 6,019,783 A | 2/2000 | Philips |
| 6,033,383 A | 3/2000 | Ginsburg |
| 6,042,559 A | 3/2000 | Dobak, III |
| 6,051,019 A | 4/2000 | Dobak, III |
| 6,096,068 A | 8/2000 | Dobak, III et al. |
| 6,110,168 A | 8/2000 | Ginsburg |
| 6,126,684 A | 10/2000 | Gobin et al. |

OTHER PUBLICATIONS

A. F. Reynolds, Jr. et al., *Intracellular recording during focal hypothermia in cat pericruciate cortex*, Experimental Neurology 46: (1975) 566–582, Academic Press, Inc.,.

J. M. Fuster and R. H. Bauer, *Visual short–term memory deficit from hypothermia of frontal cortex*, Brain Research 81: (1974) 393–400, Elselvier Scientific Publishing Company, Amsterdam, The Netherlands.

P. H. Schiller et al., *Response characteristics of single cells in the monkey superior colliculus following ablation or cooling of visual cortex*, MIT, Cambridge, Massachusetts 02139.

M. Benita and H. Conde, *Effects of local cooling upon conduction and synaptic transmission*, Brain Research 26: (1972) 133–151.

H. H. Jasper et al., *The effect of local cooling upon spontaneous and evoked electrical activity of cerebral cortex*, Canadian Journ. of Physiology and Pharmocol. vol. 47 (1970).

J. M. Fuster and G. E. Alexander, *Delayed response deficit by cryogenic depression of frontal cortex*, Brain Research 20: (1970) 85–90.

J. N. Hayward and M. A. Baker, *Diuretic and thermoregulatory responses to preoptic cooling in the monkey*, Amer. J. Physiology, 214: 4 (1968), printed in USA.

H. R. Clemo and B. E. Stein, *Effects of cooling somatosensory cortex on resonse properties of tactile cells in the superior colliculus*, Journ. Neurophysiology, 55:6 (1986) 1352–1368, printed in USA.

H. Sherk, *Area 18 cell responses in cat during reversible inactivation of area 17*, Journ. Neurophysiology, 41:1 (1978) 204–215, printed in USA.

Robert W. Rand, *Cryosurgery lesions in parkinson's disease*, Chapter 102 from Text–book of Stereotactic Functional Neurosurgery, Gildenberg and Rasher (1998).

M. Marsala et al., *Technique of selective spinal cord cooling in rat: methodology and application*, J. Nuerosci. Methods, (1997) 74: 97–106.

F. Colbourne, et al., *An automated system for regulating brain temperature in awake and freely moving rodents*, J. Neurosci. Methods, (1996) 67:185–190, Elsevier Science, Canada.

S. G. Lomber et al., *Learning and recall of form discriminations during reversible cooling deactivation of ventral–posterior suprasylvian cortex in the cat*, Proc. Natl. Acad. Sci., Neurobiology, 93: Feb. (1996) 1654–1658.

A. Simpson et al., *Thermode for deep focal cooling*, Brain Res. Bull., (1998) 21:617–621.

K. Sasaki and H. Gemba, *Effects of cooling the prefrontal and prestriate cortex upon visually initiated hand movements in the monkey*, Brain Research, (1987) 415: 462–366, Elsevier Science Publishers B.V.

Krystyna Budzinska et al., *Effects of graded focal cold block in rostral areas of the medulla*, Acta Physiol. Scand (1985), 124:329–340.

Krystyna Budzinska et al., *Effects of graded focal cold block in the solitary and para–ambigual regions of the medulla in the cat*, Acta Physiol. Scand (1985), 124:317–328.

M. Udo et al., *Cerebellar control of locomotion: effects of cooling cerebellar intermediate cortex in high decerebrate and awake walking cats*, J. Neurophysiology, 44: 1: Jul. (1980), USA.

N. S. Cherniack et al., *Graded changes in central chemoceptor input by local temperature changes on the ventral surface of medulla*, J. Physiol., (1979) 287: 191–211, Great Britain.

Robert Massarino et al., *Self–contained dual chronic cryoprobe for deep neural structures*, Physiology & Behavior, 22: 1021–1023, Pergamon Press and Brain Res. Publ., USA.

Vernon B. Brooks, *Study of brain function by local, reversible cooling*, Rev. Physiol. Biochem. Pharmacol., vol. 95 by Springer–Verlag, London, Ontario, Canada.

W. R. Patberg et al., *Blocking of impulse conduction in peripheral nerves by local cooling as a routine in animal experimentation*, J. Neurosci. Methods, (1984) 10: 267–275, Elsevier, The Netherlands.

K. Kumar et al., *Deep brain stimulation for control of intractable pain in humans, present and future: a ten–year follow–up* (Abstract), Neurosurgery, (1990) May 26(5):774–781, Department of Surgery, University of Saskatchewan,Regina, Canada. Abstract.

B. A. Simpson, *Spinal cord stimulation in 60 cases of intractable pain* (Abstract), J. Neurol. Neurosurg. Psychiatry, (1991) Mar.: 54(3): 196–199, Department of Neurosurgery, London Hospital, Whitechapel, UK. Abstract.

K. Kumar et al., *Spinal cord stimulation for chronic pain in peripheral neuropathy* (Abstract), Surg. Neurol., (1996) Oct.: 46(4): 363–369, Department of Surgery, University of Saskatchewan,Regina, Canada. Abstract.

R. R. Richardson, et al., *Spinal epidural neurostimulation for treatment of acute and chronic intractable pain: initial and long term results* (Abstract), Neurosurgery, (1979) Sep.: 5(3): 344–348. Abstract.

J. N. Campbell and D. M. Long, *Peripheral nerve stimulation in the treatment of intractable pain* (Abstract), J. Neurosurg., (1976) Dec.: 45(6): 692–699. Abstract.

J. Miles, *Pain relief: electrical stimulation* (Abstract), Nurs. Mirror, (1980) Feb. 14, 150(7): 46–47. Abstract.

K. Kumar et al., *Deep brain stimulation for intractable pain: a 15–year experience* (Abstract), Neurosurgery, (1997) Apr., 40(4): 736–746, Department of Surgery, University of Saskatchewan, Regina, Canada. Abstract.

J. Devulder, *On "Spinal cord stimulation for chronic, intractable pain: superiority of 'multi–channel' devices' by North et el., in Pain (1991) 119–130,"* (Abstract) Pain, (1991) Aug. 46(2): 236–237. Abstract.

Krishna Kumar et al., *Treatment of chronic pain by epidural spinal cord stimulation: a 10–year experience*, J. Neurosurg, (1991) 75: Sep. 402–407.

* cited by examiner

HEAT PIPE NERVE COOLER

CROSS-REFERENCE TO RELATED APPLICATIONS

This application is a continuation-in-part of the following U.S. Pat. applications: U.S. patent application Ser. No. 09/012,287, filed Jan. 23, 1998, now U.S. Pat. No. 6,051,019 and entitled "Selective Organ Hypothermia Method and Apparatus"; U.S. patent application Ser. No. 09/047,012, filed Mar. 24, 1998, now U.S. Pat. No. 5,957,963 and entitled "Improved Selective Organ Hypothermia Method and Apparatus"; U.S. patent application Ser. No. 09/052,545, filed Mar. 31, 1998, and entitled "Circulating Fluid Hypothermia Method and Apparatus"; U.S. patent application Ser. No. 09/103,342, filed Jun. 23, 1998, now U.S. Pat. No. 6,096,068 and entitled "A Selective Organ Cooling Catheter and Method of Using the Same"; U.S. patent application Ser. No. 09/215,038, filed Dec. 16, 1998, and entitled "An Inflatable Catheter for Selective Organ Heating and Cooling Catheter and Method of Using the Same"; U.S. patent application Ser. No. 09/215,040, filed Dec. 16, 1998, and entitled "Method and Device for Applications of Selective Organ Cooling"; and U.S. patent application Ser. No. 09/262,805, filed Mar. 4, 1999, and entitled "A Selective Organ Cooling Catheter with Guide Wire Apparatus".

REFERENCE TO FEDERAL FUNDING

Not Applicable.

BACKGROUND OF THE INVENTION

Pain sensation is mediated by nerve fibers. Nerve fibers extend to the brain via the spinal cord which forms a portion of the central nervous system. Referring to FIG. 1, the spinal cord 12 extends from the brain to the level of the second lumbar vertebra, at which point the spinal cord branches to numerous individual roots. Throughout the length of the spinal cord, the same is encased in the vertebral canal. Nerves 14 branch off at regular intervals.

A number of types of nerves are disposed within the posterior gray horn 16. Two types of pain sensing nerves have been identified: $A_\delta$ and C. Referring to FIGS. 2 and 3, $A_\delta$ fibers 18 are disposed within regions I and V and the same produce a rapid initial and intense response to painful stimuli. C fibers 20 are disposed within region II and produce a more blunted but prolonged response. C fibers 20 are believed to be responsible for many chronic pain syndromes.

$A_\delta$ fibers 18 and C fibers 20 are connected to the spinal cord 20 via the dorsal root 22 (referring back to FIG. 1). The dorsal root 22 is a bundle of nerves that enters the dorsal aspect of the spinal cord 12. The sensory nerves from one particular body region, such as the right leg, may be split among several dorsal root nerve bundles spaced along the length of the spinal cord 12.

Pain is conducted via fibers of the peripheral nervous system to the central nervous system, or nerves in the spinal cord. The pain signal is conducted up nerve tracts of the spinal cord to the pain sensing areas of the brain (i.e., the thalamus). The transmission of the pain signal from the peripheral nerves to the central nerves takes place in the synapses of the posterior gray horn region 16 of the spinal cord 12. A synapse is a neuron-to-neuron transmission of a signal by a chemical mediator that traverses a small gap between two axon terminals.

As noted above, many $A_\delta$ fibers 18 and C fibers 20 synapse in the most superficial, or dorsal, region of the dorsal gray horn known as zones 1 and 2. The synaptic region of the C fibers 20 is also known as the substantia gelatinosa. Various treatments directed at these fibers and these anatomical locations, can be and are used to treat pain syndromes.

An estimated 15 million Americans suffer from chronic intractable pain. 50% of persons with terminal illness have significant pain and 10% require a surgical procedure to treat the pain. $80 billion is spent annually in the United States-on chronic pain.

Current therapy for chronic pain can be divided into two categories: medical and surgical. Medical therapy is the administration of drugs ranging from Tylenol® to morphine. Morphine and its analogs are used in cases of severe pain and terminal illness. These drugs have many serious side effects such as sedation, confusion, constipation, and depression of respiration. The more severe the pain, the higher the dosage of the drug and the more significant the side effects. In addition, tolerance to these compounds develops, and escalating doses are required to achieve pain control.

Surgical therapy can range from the implantation of drug infusion devices to the ablation, or destruction, of nerves. Ablation of nervous tissue is irreversible and can cause permanent loss of function of organs and limbs. One type of surgical treatment is known as Dorsal Root Entry Zone ("DREZ") ablation. The DREZ is shown in FIG. 1 as DREZ 24. While DREZ ablation is effective at treating pain, it can also result in significant limb and organ dysfunction. Drug infusion into the spinal cord using implanted devices can reduce drug side effects, however they do not eliminate side effects entirely nor solve the problem of tolerance. These approaches require significant surgical procedures; often, terminally ill patients are not good candidates for surgery.

Nerve stimulators are also used for pain control. These electrical devices work indirectly by stimulating nerve fibers that inhibit conduction pain fibers. It is known to place devices such as nerve stimulators surgically or percutaneously and they may be placed directly adjacent to the spinal cord. For example, U.S. Pat. No. 5,643,330 to Holsheimer et al., issued Jul. 1, 1997, and entitled "Multichannel Apparatus for Epidural Spinal Cord Stimulation", discloses placing an epidural spinal cord stimulator adjacent to spinal cord dura mater.

Stimulators are relatively ineffective in controlling pain. This may be in part due to the indirect mechanism of action. Further, they can cause dysthesias and paresthesias (neurologenic pain) due to the stimulation of nerve fibers.

There is a need for a method and apparatus to combat pain, especially chronic pain, which do not suffer from the drawbacks of current medical and surgical therapies.

SUMMARY OF THE INVENTION

In one aspect, the invention is directed to a method of cooling a portion of a spinal cord of a patient. The method includes delivering a portion of a heat pipe to a spinal cord of a patient, the heat pipe including an evaporator and a condenser, including disposing the evaporator at least in partial thermal communication with the spinal cord. The evaporator is cooled by passing a working fluid between the evaporator and the condenser.

Implementations of the invention may include one or more of the following. The delivering may further include disposing the evaporator at least in partial thermal communication with the dorsal root entry zone of the spinal cord. The working fluid may be passed between the evaporator and the condenser through a conduit, and the conduit may be a tube or wick structure, for example. The condenser may be implanted within a patient or may be located externally of a patient. The condenser may have an insulated lower chamber into which the conduit enters and an upper chamber into which the return tube enters, the lower and upper chambers separated by a porous structure, and may further include passing the working fluid in gaseous form from the evaporator through the return tube within the conduit to the upper chamber, condensing the working fluid at least partially from the gaseous form into the liquid form, passing the working fluid from the upper chamber to the lower chamber through the porous structure, and passing the condensed working fluid from the lower chamber to the evaporator through the conduit. Another implementation may include disposing the upper chamber in thermal communication with a cold source. The evaporator may be disposed adjacent the dura mater, or between the spinal cord and the dura mater, or on the side of the dura mater opposite the spinal cord.

In another aspect, the invention is directed to an apparatus for cooling a portion of tissue. The apparatus includes an evaporator to be placed in thermal communication with a portion of tissue; a condenser disposed in thermal communication with a source or sink of heat, the condenser including an upper chamber and a lower chamber; and a conduit disposed between the evaporator and the condenser, the conduit including a wick structure, to communicate working fluid between the two. An implementation of the invention may include providing a porous structure to separate the lower chamber from the upper chamber.

Advantages of the invention include one or more of the following. The invention provides for control of chronic pain in an effective manner. The processes used to achieve hypothermia to control pain are reversible. Nerve tissue is not destroyed as in certain other techniques. Nerve tissue recovers completely when the processes are stopped. The invention allows for treatment of not only chronic pain but also urge incontinence, muscle spasticity, epilepsy, and may even be of benefit in treating multiple sclerosis.

DETAILED DESCRIPTION OF THE PREFERRED EMBODIMENTS

The invention provides, in one embodiment, a cooling catheter or cooling patch that can be placed on nerve fibers or tissue. When nerve tissue is cooled (+2° to +20° C.), conduction therethrough is stopped. Synaptic transmission is susceptible to termination by cooling, with near complete blockage of pain transmission occurring at +20° C. A $\delta$fibers are more susceptible to reduction of conduction via cooling and will be affected by warmer temperatures than C-fibers. For example, some $A_\delta$ fibers will cease to conduct at +8° C. whereas the conduction of some C-fibers is substantially blocked at +3° C. This conduction block is known to be reversible. Normal conduction returns once the nerve warms.

Figure 1:
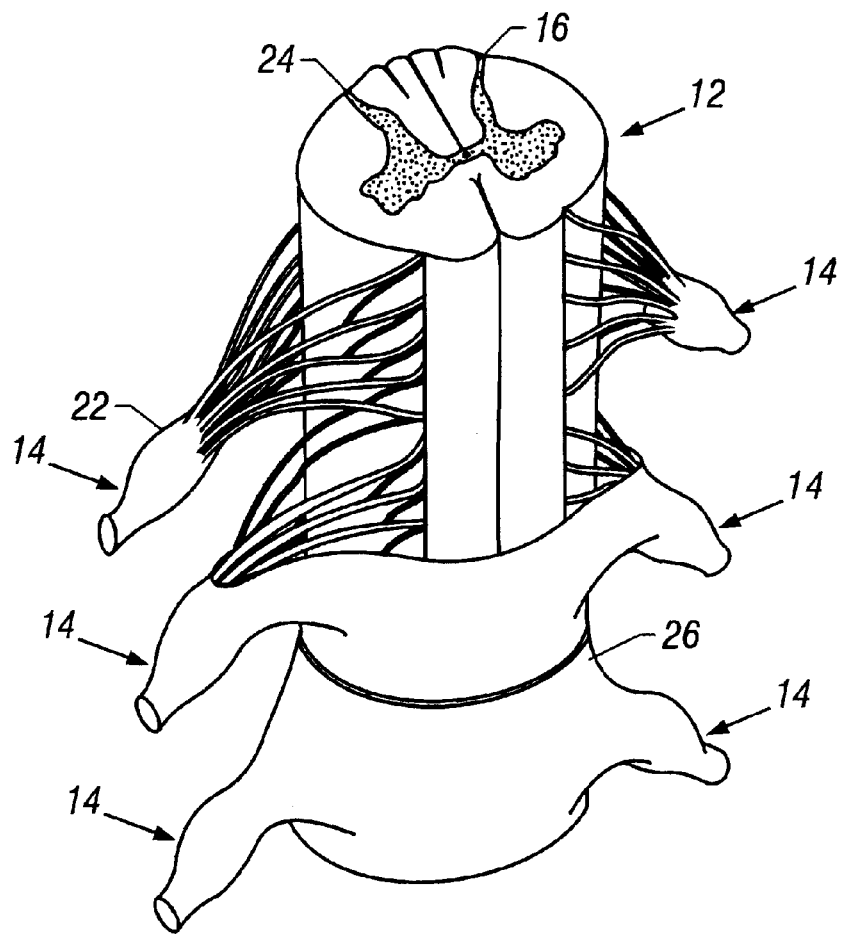
FIG. 1 is a schematic drawing of the spinal cord.

In one method of controlling pain, described in more detail below, the cooling patch or catheter is placed parallel along the dorsal root entry zone 24 in contact with the spinal cord 12 or on the dura 26, a membrane that surrounds the cord (see FIGS. 1 and 9). The cooling section of the catheter or patch could be 5 to 10 cm long, or greater, and would stretch along several or many DREZs. This would substantially ensure the treatment of all pain fibers for a given body area that is the source of pain.

Figure 2:
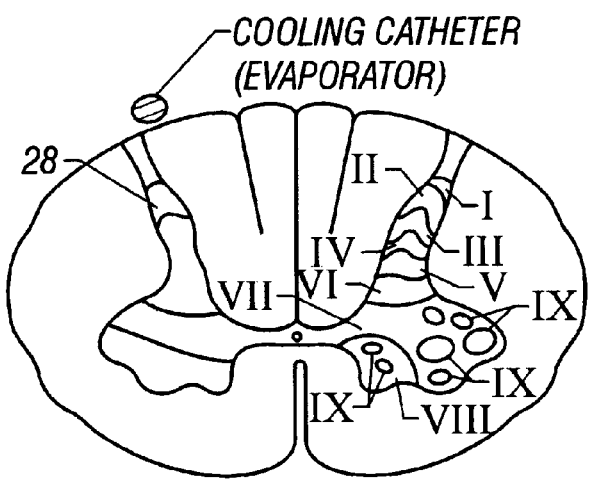
FIG. 2 is a schematic cross-section of the spinal cord showing the anterior and posterior gray horn.
Figure 3:
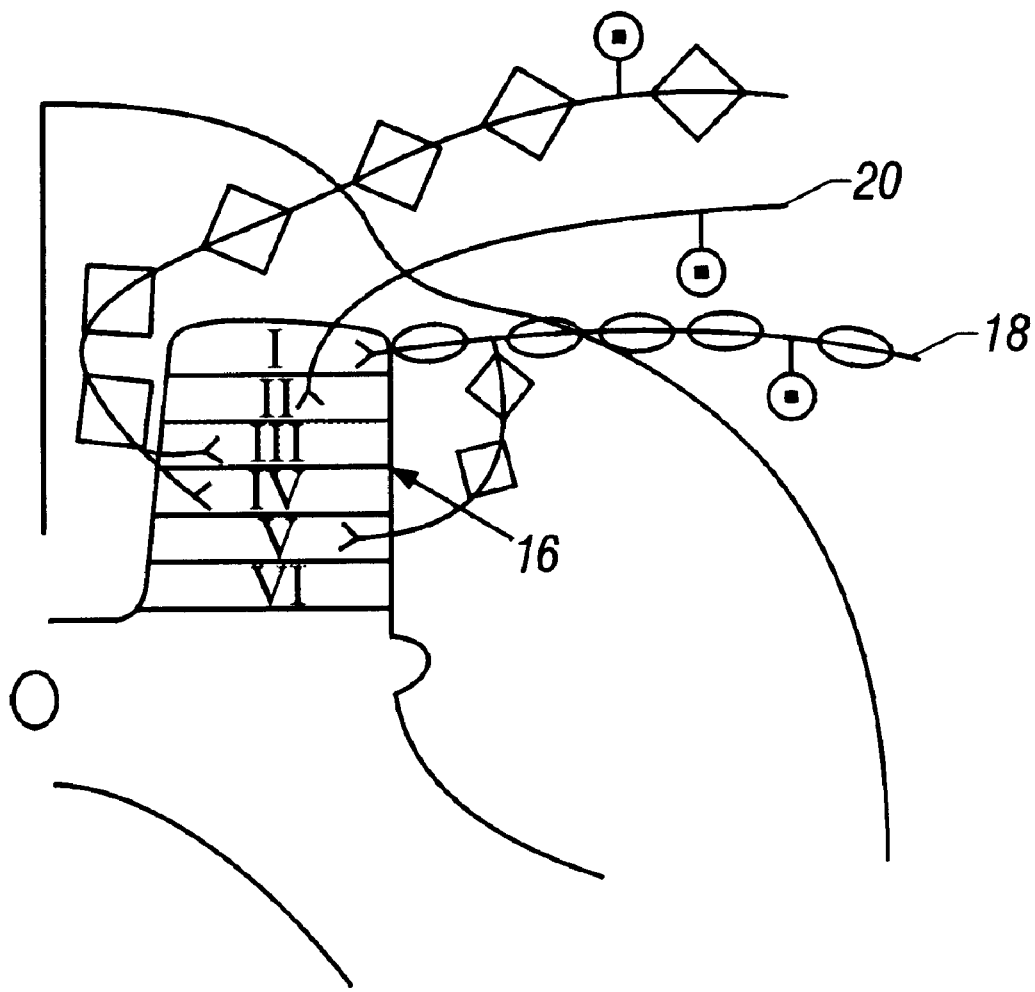
FIG. 3 is more detailed schematic cross-section of a portion of the spinal cord, showing the posterior horn and layers of nerve fibers therein.

By placing the cooling device in the spinal cord 12, the synapses at the DREZ can be affected. Since these synapses are susceptible to termination or reduction of conduction at relatively warm temperatures, the temperature of the cooling device can be maintained at a reasonably warm temperature. For example, the surface of the cooling catheter may be maintained at +5° to +10° C. to produce cooling to +20° C. at the depth of the substantia gelatinosa 28 (FIG. 2), or 2–3 mm, at the DREZ 24.

Figure 4:
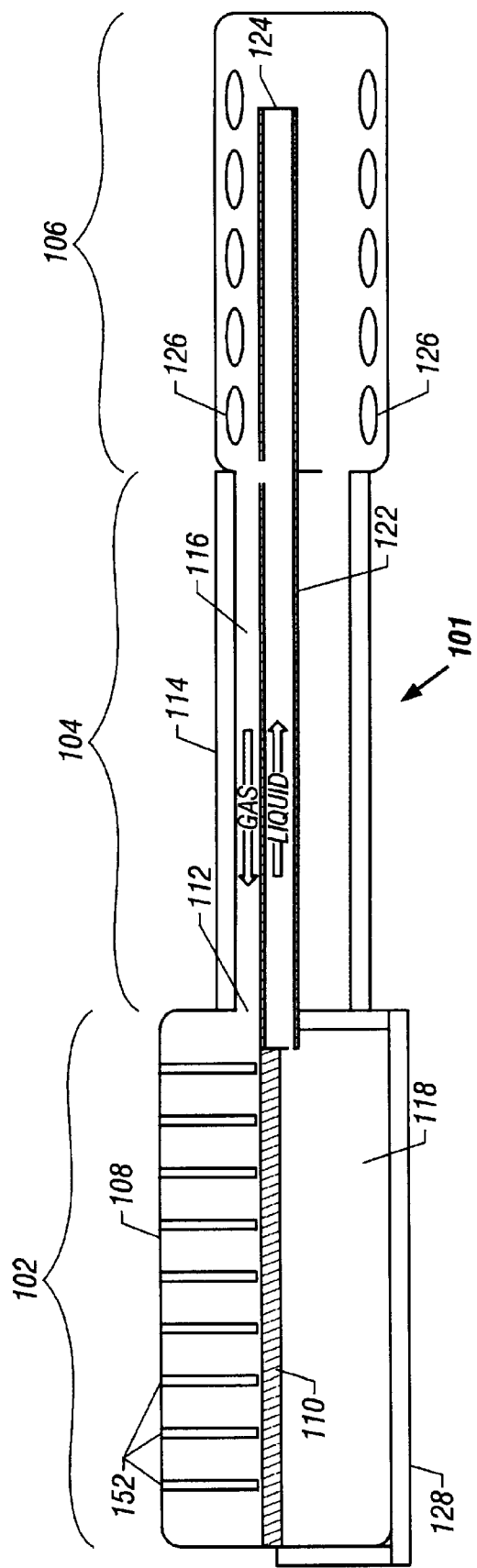
FIG. 4 is a schematic cross-sectional side view of an embodiment of the invention, which may be implanted into a patient suffering chronic pain.

One method of cooling employs a passive two-phase heat transfer device, or heat pipe. Referring to FIG. 4, a heat pipe 101 includes three basic parts: an evaporator 106, an intervening connecting conduit 104, and a condenser 102. The evaporator 106 and the condenser 102 are connected to each other by the conduit 104.

Figure 5:
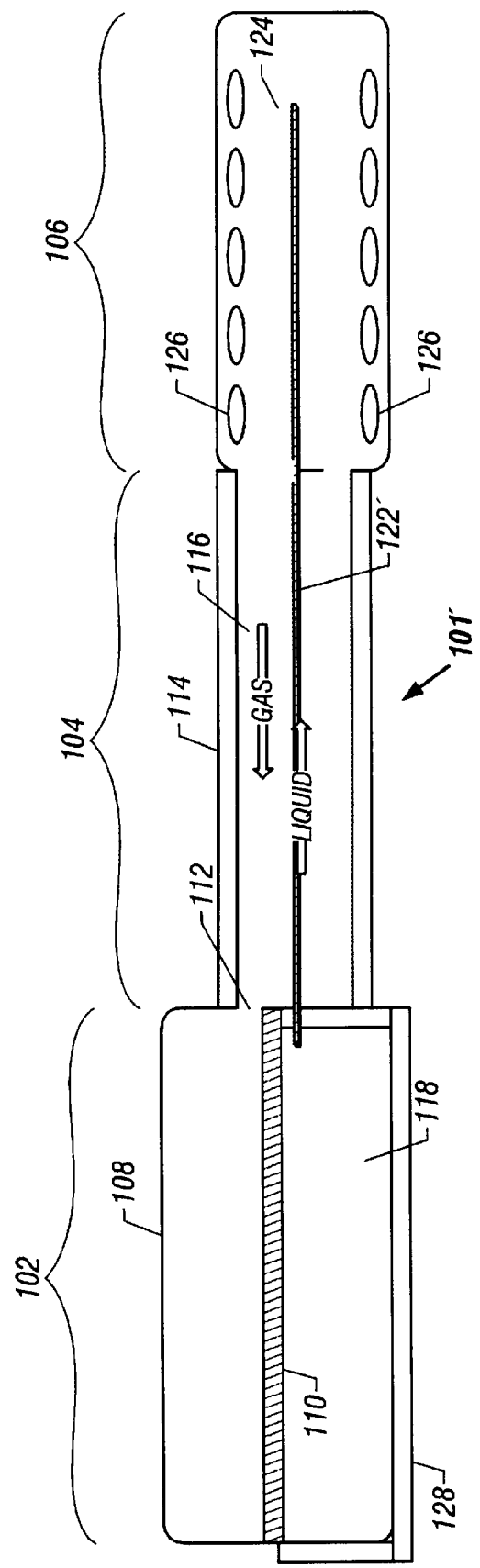
FIG. 5 is a schematic cross-sectional side view of an alternative embodiment of the invention, which may be implanted into a patient suffering chronic pain.
Figure 6:
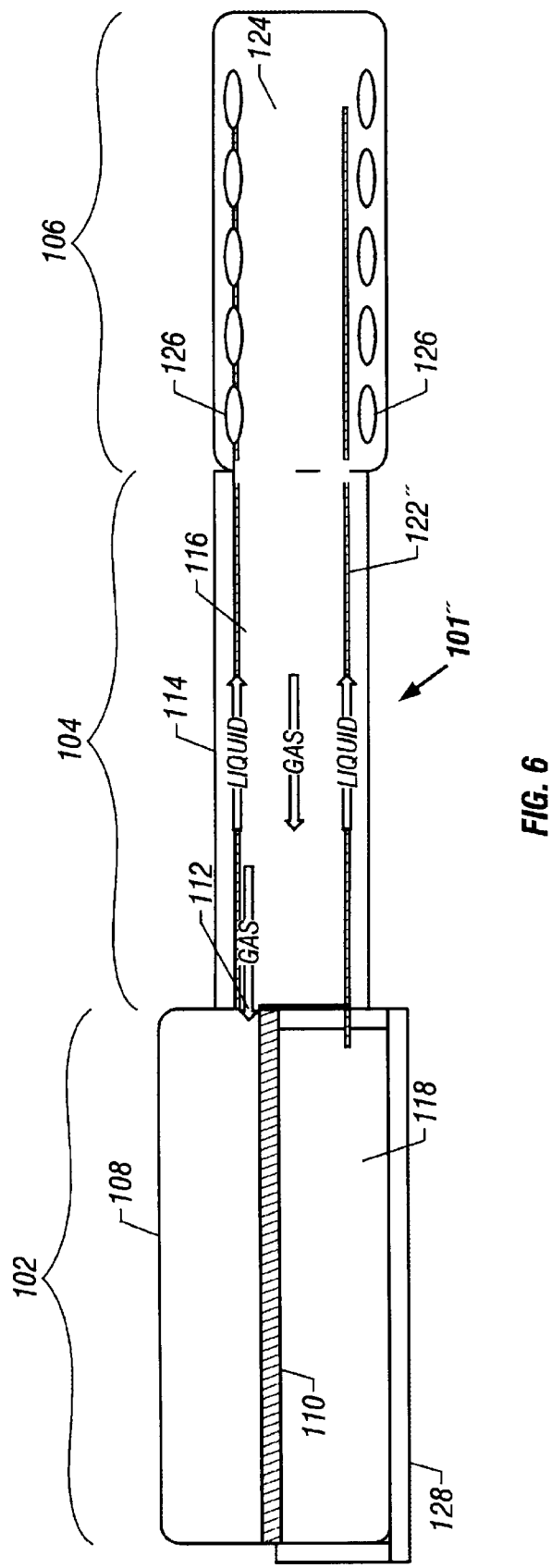
FIG. 6 is a schematic cross-sectional side view of another alternative embodiment of the invention, which may be implanted into a patient suffering chronic pain.

The conduit 104, which is insulated, allows a coolant to flow between the evaporator 106 and the condenser 102. The conduit 104 may employ a variety of structures. In FIG. 4, a capillary tube 122 is shown in which coolant flows by capillary forces. In FIG. 5, a conventional wick structure is shown. In FIG. 6, a cylindrical wick structure with a central return lumen is shown. In general, as shown in FIGS. 4–6, the conduit 104 includes a tube 114. Tube 114 defines a return path for gaseous coolant as will be described below.

In the heat pipe 101, heat enters from the body tissue and is absorbed by the evaporator 106. A liquid coolant such as a freon, within the evaporator 106, boils and absorbs the heat input, resulting in cooling. The vaporized freon then returns to the condenser 102 via a return tube 116 defined by tube 114 within the conduit 104. At the condenser 102, heat is removed, either by ambient air heat exchange or by cooling from another source. The cooled coolant condenses the gaseous coolant and the same then flows back down the conduit 104 to the evaporator 106.

The condenser 102 may be a small hollow metallic disc made from titanium, stainless steel, or other similar metals. The disk acts as a condenser and reservoir for a freon or other such working fluid. The disc has two chambers, an upper chamber 108 and a lower chamber 118. The lower chamber 118 may be insulated by an evacuated space 128 or other such insulation. There is no insulation on the upper chamber 108 of the disk or condenser 102. A porous/sintered disk 110 may optionally be used to separate the two halves. The conduit 104 enters the insulated lower chamber 118 or porous structure or disc 110. The evaporator conduit 116 enters the upper chamber 108 (i.e., the uninsulated half of the disk). The connection of the evaporator conduit 116 into the upper chamber 108 is indicated in FIGS. 4–6, although some details of the connection are omitted for clarity. At least one heat transfer fin 152 may be provided within the upper chamber to assist in the conduction of heat away from porous structure 110 to the cold source described below (for clarity, this fin 152 is only shown in FIG. 4).

In FIG. 4, the conduit 104 includes a capillary tube 122. The capillary tube 122 causes capillary forces to move the liquid coolant from the condenser 102 to the evaporator 106. The liquid inlet to the capillary tube 122 may be entirely within a lower chamber 118, described in more detail below, entirely within a porous disc 110, described in more detail above, or partly in both. In FIG. 4, the last embodiment is shown. In other words, liquid coolant may enter tube 122 through either of the porous disc 110 or the lower chamber 118.

In FIG. 5, the conduit 104 includes a wick structure 122'. The wick structure "wicks" the liquid coolant to the evaporator 106. Of course, it is understood that wick structures also employ capillary action, but in this embodiment the wick structure is distinguished from a capillary tube per se. Like the embodiment of FIG. 4, the wick structure 122' may be connected either to the lower chamber 118, porous disc 110, or both. Also in this embodiment, the lower chamber 118 should be sealed so that only wick structure 122' (and of course porous disc 110) may be inlets and outlets. In other words, evaporated gaseous coolant should be prohibited from entering lower chamber 118. The same is true of capillary tube 122.

In FIG. 6, a cylindrical wick structure 122" is shown that provides an additional embodiment of the invention. In this embodiment, the wick structure 122" approximately matches the inner diameter of the conduit 104. In this way, the wick structure 122" is provided with more surface area and volume with which to wick coolant. The same travels down the wick structure 122" to the evaporator. Once evaporated, the gaseous coolant may travel in the central lumen 116 defined by the wick structure 122" itself back to the condenser 102. Of course, the wick structure 122" in this embodiment is shaped such that coolant may reach even the upper portions of the wick structure 122" (adjacent upper chamber 108) without entering the upper chamber 108. Nevertheless, most of the coolant may still travel along the portion of the wick structure adjacent the lower chamber 118. As above, the wick structure may contact the lower chamber 118 (as shown in FIG. 6) or may alternatively contact the porous disc 110, or both.

The evaporator 106 may be, e.g., a 1–2 mm outer diameter catheter disposed along the spinal cord, and may be, e.g., 10 to 15 cm in length. The evaporator 106 may have metal foil windows 126 that respectively align with the plurality of DREZ 24 thereby enhancing heat transfer. The evaporator 106 catheter can be made from polyimide and the metal foil windows 126 may be made of platinum or platinum iridium. It should be clear to one of skill in the art that the relative dimensions of the evaporator 106 in FIGS. 4–6 are greatly exaggerated and that most feasible such evaporators would have a ratio of length to width that is much greater than that shown in the figures.

The evaporator 106 is connected to the condenser 102 by the conduit 104. The conduit may reside in the tissue between the skin and the spinal cord. An end of the conduit 104 distal of evaporator 106 may be located between the skin and the spinal cord, and more preferably near the skin so as to allow thermal energy to be passed from the skin to the conduit and condenser, as well as vice-versa. In a separate embodiment, described in more detail below, conduit 104 may extend through a percutaneous incision to a region external of the body. It is also noted that the evaporator 106 may include a portion of the conduit 104 for better delivery of the coolant to the heat transfer portions of the evaporator.

In use, the evaporator 106 is inserted along and adjacent to the spinal cord 12 percutaneously with a needle introducer. The needle introducer allows the evaporator 106 to be disposed within the vertebra so as to be in thermal communication with the spinal cord 12. In this context, thermal communication refers to the ability of the evaporator 106 to absorb heat from the spinal cord 12. This thermal communication may arise from conduction, convection, or radiation. The evaporator 106 is slid along the spinal cord so as to achieve a high mutual surface area of contact.

Figure 7:
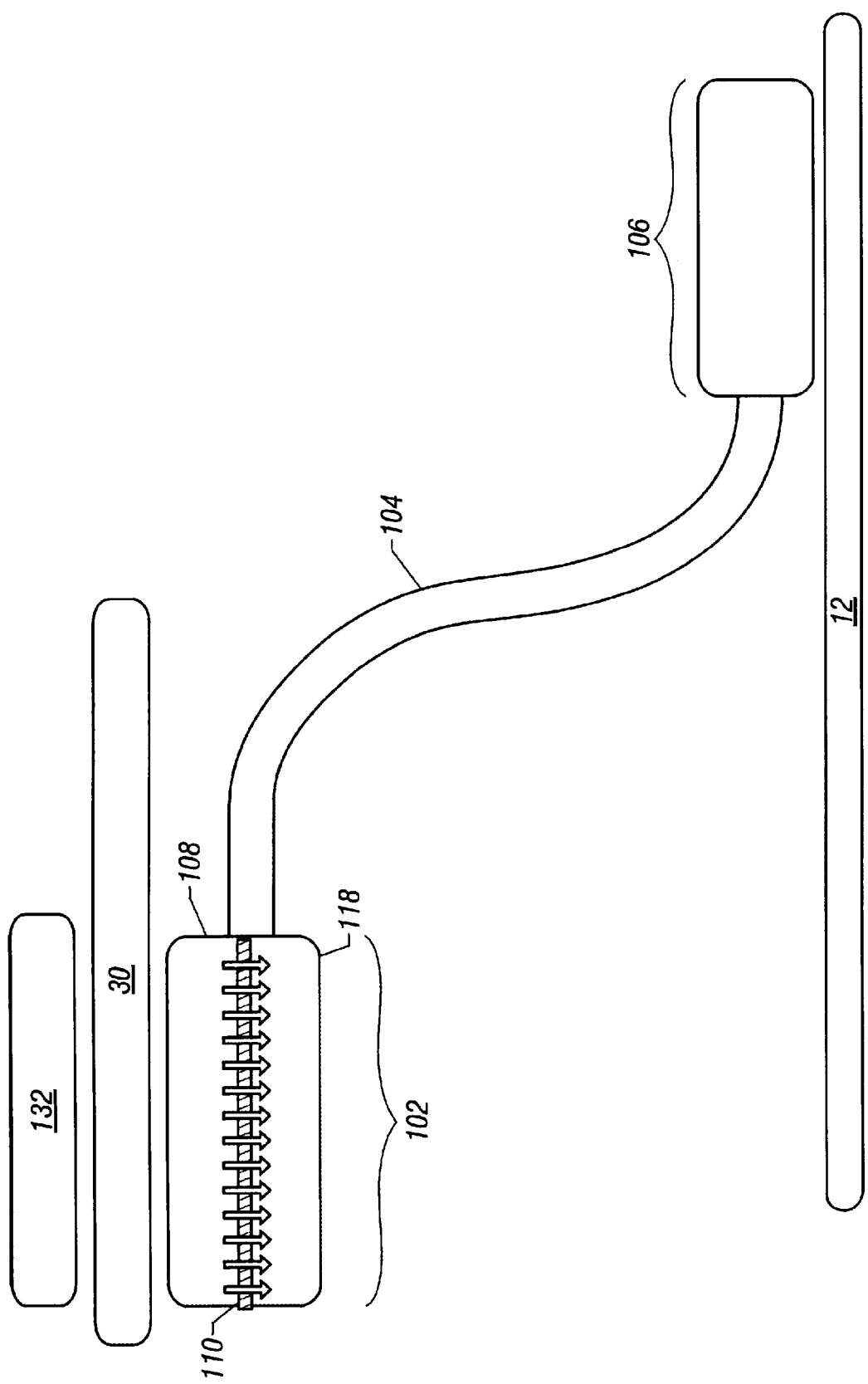
FIG. 7 is a schematic view of the embodiments of the invention shown in FIGS. 4–6 including a schematic of the same's placement within a patient.

Referring to FIG. 7, the condenser 102 is implanted just beneath the skin 30 with the uninsulated side (chamber 108) facing outward just underneath the skin 30. One way in which to start the cooling process is to place a cold pack 132 over the skin 30 adjacent the condenser 102. The cold pack 132 may be a thermoelectric cooler or an ice bag. Because the upper half (chamber 108) is uninsulated, it is cooled by the cold pack 132. The coldness condenses the coolant, which subsequently wicks through the porous separator 110 and enters the lower insulated half of the disk. Because the lower half (chamber 118) is insulated, the heat from the body does not allow the coolant to boil. It is noted that only a portion of the insulation of the lower chamber is shown in FIG. 7, for clarity. The coolant then flows down the capillary within conduit 104 to the evaporator 106 where it boils and cools the nerve tissue. The gaseous coolant returns to the upper chamber 108 of the condenser where it is cooled and liquefied, restarting the process. Removing the cold pack 132 terminates the cooling.

Figure 8:
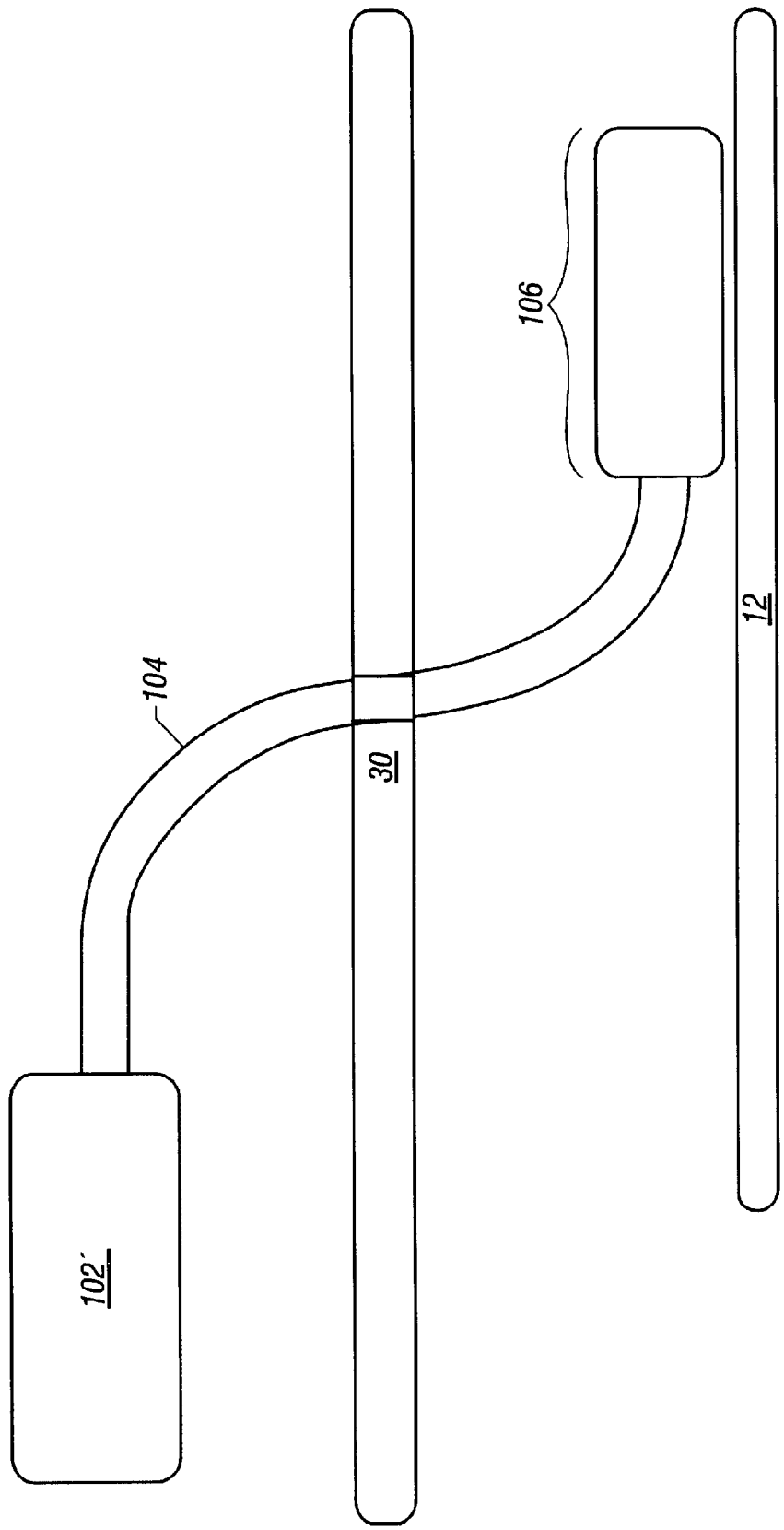
FIG. 8 is a schematic view of an alternative embodiment of the invention including a schematic of the same's placement within a patient.

In an alternative embodiment, shown in FIG. 8, the condenser 102 is replaced with a cooling unit 102' that is resident outside the body. In this embodiment, cooling unit 102' provides and cycles a working fluid down a conduit to evaporator 106. Evaporator 106 may be similar in most or all aspects to the evaporator in previous embodiments. The coolant or working fluid flows back to cooling unit 102' via a return tube. The conduit and return tube may be similar to the conduit and return tube described above.

In any of the embodiments, the coolant or working fluid may be a freon or other such type of refrigerant. In the alternative embodiment of FIG. 8, the working fluid may also be saline or other similar coolants. Saline may be employed in this embodiment at least in part because this embodiment need not rely on evaporation and condensation to propel the working fluid: rather, the cooling unit may supply the required pressure.

Figure 9:
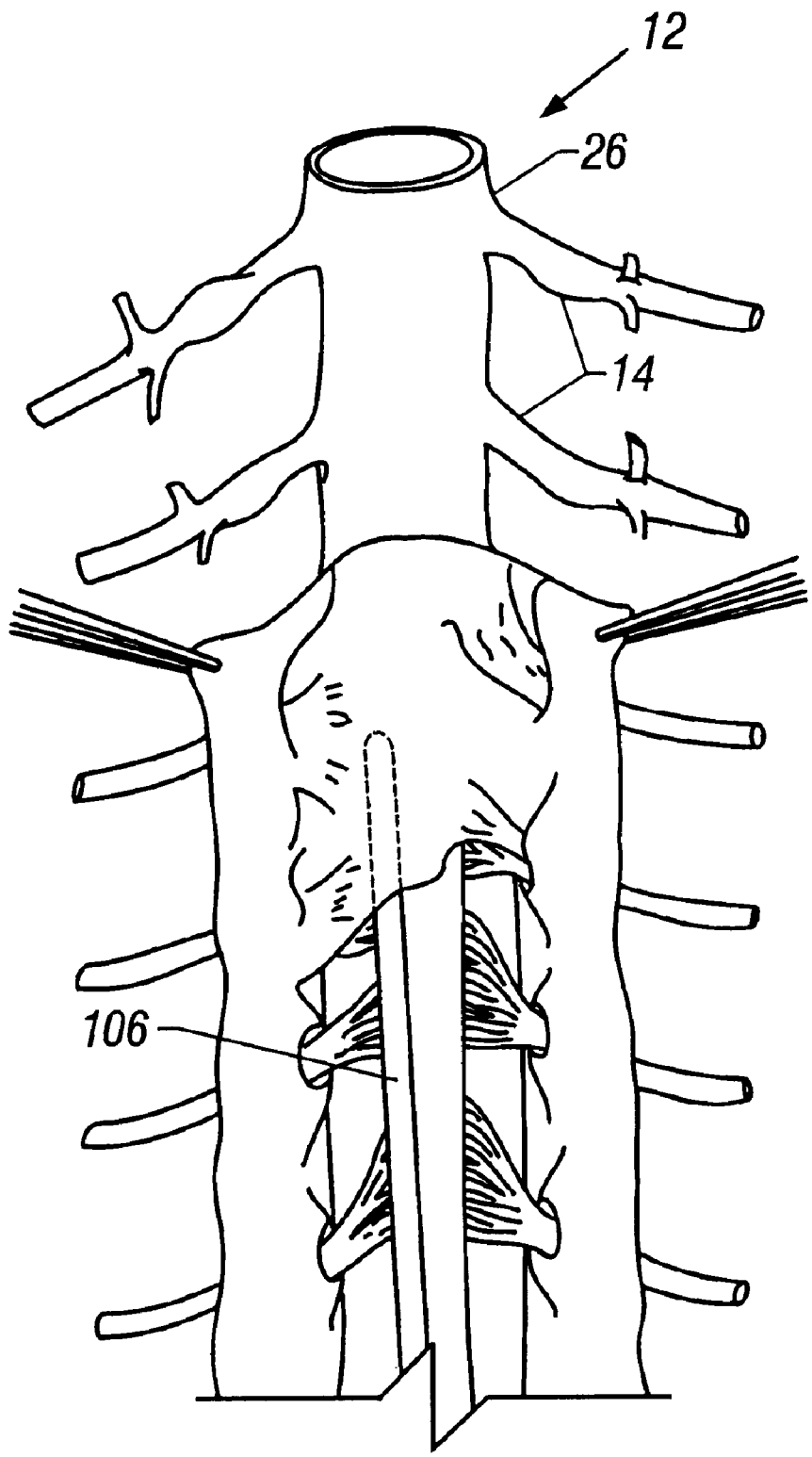
FIG. 9 is a more detailed schematic view of the placement of the invention alongside a patient's spinal cord.

FIG. 9 shows one possible placement of the evaporator 106 along the spinal cord 12. In FIG. 9, the evaporator 106 is disposed along the spinal cord 12 subdurally, i.e., under the dura mater. It should be noted that the evaporator 106 may additionally be disposed epidurally, i.e., outside but adjacent to the dura mater.

While the invention has been described with respect to certain embodiments, it will be clear to those skilled in the art that variations of these embodiments may be employed which still fall within the scope of the invention. Accordingly, the scope of the invention is limited only by the claims appended hereto.

What is claimed is:

1. A method of cooling a portion of a spinal cord of a patient, comprising:
   delivering a portion of a heat pipe to a spinal cord of a patient, the heat pipe including an evaporator and a condenser, including disposing the evaporator at least in partial thermal communication with the spinal cord; and
   cooling the evaporator by passing a working fluid between the evaporator and the condenser.

2. The method of claim 1, wherein the delivering further comprises disposing the evaporator at least in partial thermal communication with the dorsal root entry zone of the spinal cord.

3. The method of claim 1, further comprising passing the working fluid between the evaporator and the condenser through a conduit.

4. The method of claim 3, wherein the conduit is a tube.

5. The method of claim 3, wherein the conduit is a wick structure.

6. The method of claim 3, further comprising implanting the condenser within the patient.

7. The method of claim 3, further comprising locating the condenser externally of the patient.

8. The method of claim 6, wherein the condenser has an insulated lower chamber into which the conduit enters and an upper chamber into which the return tube enters, the lower and upper chambers separated by a porous structure, farther comprising passing the working fluid in gaseous form from the evaporator through the return tube within the conduit to the upper chamber, condensing the working fluid at least partially from the gaseous form into the liquid form, passing the working fluid from the upper chamber to the lower chamber through the porous structure, and passing the condensed working fluid from the lower chamber to the evaporator through the conduit.

9. The method of claim 8, further comprising disposing the upper chamber in thermal communication with a cold source.

10. The method of claim 1, further comprising disposing the evaporator adjacent the dura mater.

11. The method of claim 10, further comprising disposing the evaporator between the spinal cord and the dura mater.

12. The method of claim 10, further comprising disposing the evaporator on the side of the dura mater opposite the spinal cord.

* * * * *